United States Patent [19]

Kronberg

[11] Patent Number: 5,198,870

[45] Date of Patent: Mar. 30, 1993

[54] ATOMIC LINE EMISSION ANALYZER FOR HYDROGEN ISOTOPES

[76] Inventor: James W. Kronberg, 108 Independent Blvd., Aiken, S.C. 29801

[21] Appl. No.: 697,032

[22] Filed: May 8, 1991

[51] Int. Cl.$^5$ .................................................. G01J 3/30
[52] U.S. Cl. .................................... 356/311; 356/326; 356/328
[58] Field of Search ............... 356/311, 313, 326, 328, 356/416

[56] References Cited

U.S. PATENT DOCUMENTS

| | | | |
|---|---|---|---|
| 3,348,447 | 10/1967 | Goleb | 356/416 |
| 3,612,686 | 10/1971 | Braman | 356/86 |
| 3,627,421 | 12/1971 | Harley | 356/98 |
| 3,973,118 | 8/1976 | LaMontagne | 250/226 |
| 4,255,051 | 3/1981 | Imamura et al. | 356/306 |
| 4,723,438 | 2/1988 | Adler-Golden et al. | 73/23 |
| 4,766,318 | 8/1988 | Adler-Golden et al. | 250/385.2 |
| 4,798,464 | 1/1989 | Boostrom | 356/328 |
| 4,898,465 | 2/1990 | Crawford et al. | 356/311 |
| 5,050,991 | 9/1991 | Welch | 356/328 |

Primary Examiner—F. L. Evans
Assistant Examiner—K. P. Hantis
Attorney, Agent, or Firm—Harold M. Dixon; William R. Moser; Richard E. Constant

[57] ABSTRACT

Apparatus for isotopic analysis of hydrogen comprises a low pressure chamber into which a sample of hydrogen is introduced and then exposed to an electrical discharge to excite the electrons of the hydrogen atoms to higher energy states and thereby cause the emission of light on the return to lower energy states, a Fresnel prism made at least in part of a material anomalously dispersive to the wavelengths of interest for dispersing the emitted light, and a photodiode array for receiving the dispersed light. The light emitted by the sample is filtered to pass only the desired wavelengths, such as one of the lines of the Balmer series for hydrogen, the wavelengths of which differ slightly from one isotope to another. The output of the photodiode array is processed to determine the relative amounts of each isotope present in the sample. Additionally, the sample itself may be recovered using a metal hydride.

18 Claims, 2 Drawing Sheets

ATOMIC LINE EMISSION ANALYZER FOR HYDROGEN ISOTOPES

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to isotopic analysis. In particular, the present invention is a method and apparatus for determining the relative amounts of isotopes of hydrogen by atomic line emission spectra.

2. Discussion of Background

Isotopic analysis of hydrogen is used throughout the nuclear industry and, in particular, in processes where two isotopes of hydrogen, deuterium and protium, or their compounds, heavy water and ordinary water, respectively, must be separated or kept separated. Such processes include heavy water refining and reprocessing, environmental testing (in which deuterium may be used as a non-radioactive tracer), and monitoring of heavy water reactor moderator for possible light water contamination. Similarly, in the processing of the third isotope of hydrogen, tritium, isotopic analysis is needed to monitor the purity of the product and to guard against contamination by either of hydrogen's lighter isotopes. In some cases, it is necessary to detect even very small amounts of one hydrogen isotope in the presence of very much larger amounts of another.

Most hydrogen isotopic analysis is currently performed using mass spectroscopy: a sample is injected into a vacuum chamber, where its atoms are ionized and accelerated in one direction, forming a beam. After moving through a combination of electric and magnetic fields, the ions in the beam are sorted out according to their mass, charge and velocity, with some of them being steered into a detector. By varying field strengths, it is possible to steer first one and then another part of the beam into the detector, and measure the relative number of ions in each part.

Mass spectroscopy is a cumbersome process, requiring equipment which typically costs several tens of thousands of dollars. The magnets are heavy and bulky, and must be set up very precisely so as to generate fields of uniform and well-known characteristics. Constant pumping is needed to maintain a high-quality vacuum (about $10^{-6}$ mm Hg) inside the chamber, all the while the sample material is continuously being injected into it, and notwithstanding the inevitable leaks and outgassing of system components. High ion-accelerating voltages are needed, creating a possible hazard for operators and maintenance people. Additionally, health risks, not yet fully understood, have been associated with strong magnetic fields.

Because the vacuum system must be pumped down thoroughly between samples and because each sample is analyzed literally "atom-by-atom", the method is slow. Further delays result from the fact that, due to the high cost, a single mass spectroscope must often be shared among several different experiments or sampling points. Hence, mass spectroscopy is not well-suited to real time applications such as advanced process control.

Mass spectroscopy is further limited in that it cannot readily separate isotopes of similar mass but different atomic number. While this is not a major problem in most hydrogen isotopic analyses, it is significant in the case of tritium since its decay product is helium 3. In some cases, charged molecules can also "masquerade" as ions of heavier isotopes: for instance, HD+ for tritium. There remains a need for a simple, effective apparatus for the isotopic analysis of hydrogen.

SUMMARY OF THE INVENTION

According to its major aspects and broadly stated, the present invention is an apparatus for isotopic analysis of a sample of hydrogen gas. The apparatus is designed to excite to higher energy states the electrons of a sample of hydrogen that may have one, two or three of its isotopes present and, as the electrons return from higher energy states to lower and emit light energy as they do, sort out the different wavelengths of the light and quantify the amount of light of each wavelength. These wavelengths are specific to hydrogen atoms, so that charged molecules or He-3 atoms cannot interfere, and differ slightly from one isotope to another.

The apparatus comprises a chamber having an interior that receives the gas sample, means for introducing the gas sample into the chamber, means for exciting at least some of the electrons in the sample to higher energy states so that those electrons emit light on their return transition from the higher to lower energy states, filters for passing the desired portion of the wavelengths of light from the chamber, distributing means such as a Fresnel prism, that receives the portion of light passed by the filters and disperses it according to wavelength to a lens system and ultimately to a detecting means that detects the amounts of light as a function of wavelength. The detecting means is preferably an array of photodiodes that produces a corresponding output which is then processed. The apparatus also preferably includes a means for recovering the gas sample, such as a metal hydride bed conveniently located near the chamber.

The Fresnel prism is preferably composed of a stack of alternating layers of materials, a first material with saw-tooth ridges in it followed by a second, filling material. Both materials have substantially the same refractive index, but different dispersions, in the wavelength band of interest. One of these dispersive materials is most preferably selected from materials that are anomalously dispersive in the region near the wavelength of interest so that the ability of each layer to contribute to the dispersion of the light is maximized and absorption of the light is minimized.

The Fresnel prism is an important feature of the present invention. In its preferred embodiment, it enables sufficient dispersion to take place in a small space by taking advantage of anomalous dispersion of the wavelengths of interest, while minimizing the strong light absorption usually associated with anomalous dispersion. Because of its impact on reduction of path length, this prism substantially simplifies the design and manufacture of the overall apparatus.

Another important feature of the present invention is the use of atomic emission spectrum lines that result from exposure of a hydrogen sample to an electrical discharge at moderately low pressure to determine the isotopic content of a sample. This feature makes it possible to distinguish the isotopes of hydrogen and quantify them without using a mass spectroscope of high-vacuum equipment, but, rather, with less elaborate, less costly equipment.

Yet another feature of the present invention is the recovery of the sample itself by use of metal hydrides. Especially if the sample contains tritium or deuterium, recovery is important because of the radioactive nature of tritium and the cost of production of both isotopes.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
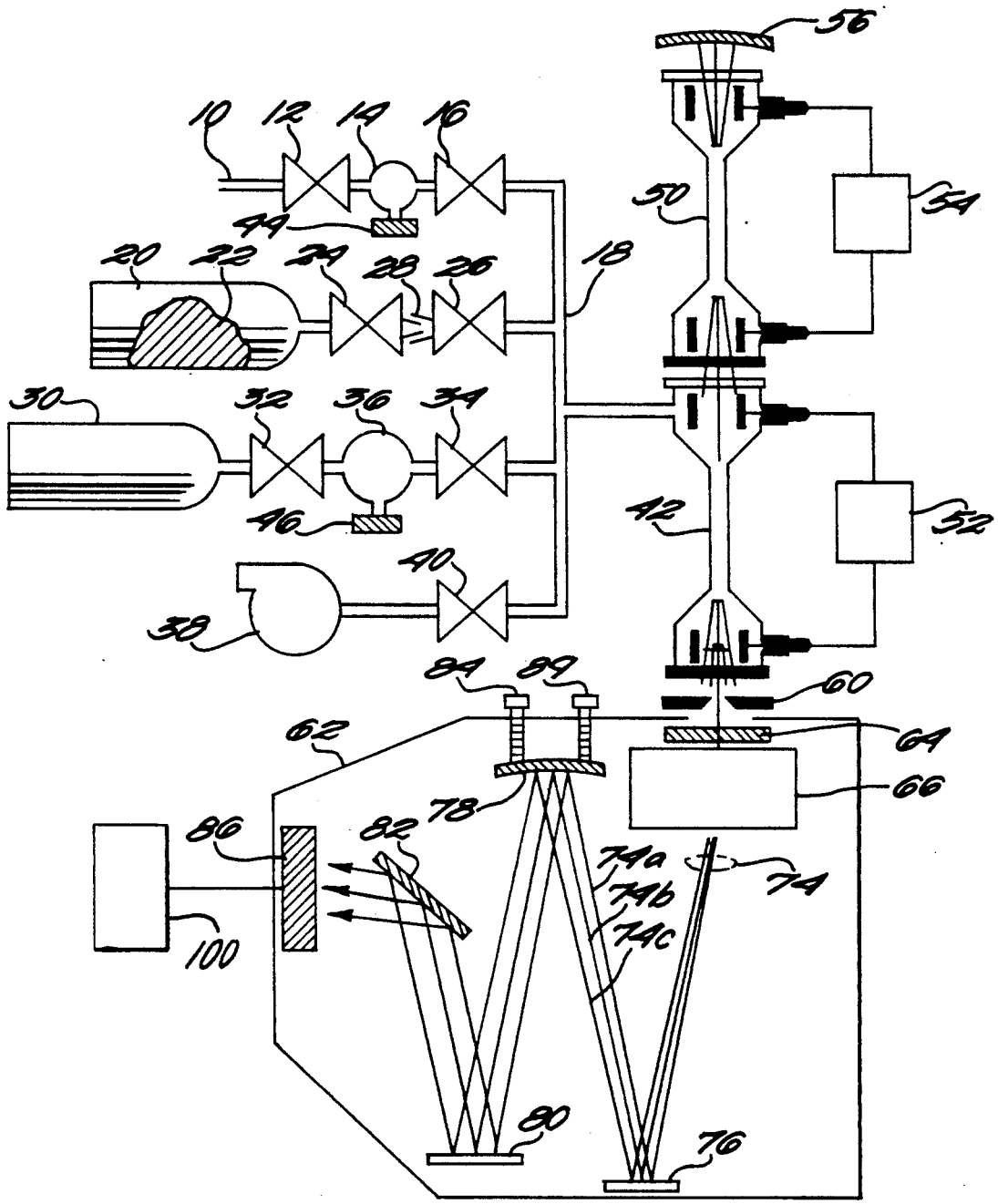
FIG. 1 is a schematic view of apparatus according to a preferred embodiment of the present invention.

There is a little-recognized property of the light emitted by isolated hydrogen atoms. When placed in a glass tube at a pressure around 1 mm Hg and exposed to a high-voltage discharge at limited current, hydrogen gives off light at specific wavelengths ranging from the far ultraviolet to the deep infrared. These wavelengths fall into a theoretically infinite number of series, each series characterized by a dominant long-wavelength line followed by infinitely many lines at shorter wavelengths, each subsequent line being progressively dimmer and closer together until they can no longer be distinguished, but ending at a well-defined limiting wavelength. The first five of these series for hydrogen are named for their discoverers (in order from shortest wavelength to longest: Lyman, Balmer, Paschen, Brackett and Pfund); other series, lying deeper in the infrared and largely overlapping, are unnamed.

The pattern was first noticed in the Balmer series, the dominant spectral lines of which fall in the visible part of spectrum. The Balmer lines include an $\alpha$ line at 656.28 nm, a $\beta$ line at 486.13 nm, a $\gamma$ line at 434.05 nm, a $\delta$ line at 410.17 nm, an $\epsilon$ line at 397.01 nm, a $\zeta$ line at 388.91 nm, and so on to a series limit at 364.56 nm. Balmer derived an equation for predicting their wavelengths, and this equation was later generalized by Rydberg to fit all other spectral lines emitted by hydrogen under these conditions:

$$1/\lambda = \mathscr{R}[1/n^2 - 1/m^2]$$

where m and n are integers, m is larger than n, and $\mathscr{R}$ is the "Rydberg Constant", experimentally measured at 10967757.6 wavelengths per meter.

With the development of quantum theory, it was shown that this explanation is consistent with a single atom model in which the electron's angular momentum is quantized and only certain orbital radii and energies are permitted.

Bombardment of rarified hydrogen gas by electrons (or other radiation) adds energy, breaking the molecules apart and ionizing the individual atoms. These atoms then recapture electrons, but in most cases an electron does not have to move immediately into the lowest and most stable energy state (n=1). Instead, it moves downward through a number of states in succession. With each transition, the excess energy is given off as a single quantum of light. Because the wavelength of such a quantum is inversely proportional to its energy, small transitions yield long infrared wavelengths, and large transitions, short ultraviolet ones. In this way, all of the observed spectral lines and series are generated.

While Rydberg assumed the measured factor $\mathscr{R}$ to be constant, Urey and others have shown that it is not. Instead, $\mathscr{R}$ is proportional to the electron's effective or reduced mass, which is determined in part by the mass of the nucleus it orbits:

$$\mathscr{R} = m_n \mathscr{R} inf / [m_e + m_n]$$

As a result, the wavelength of the emission line resulting from the electron transition between a given m and n will vary slightly, depending on whether the emitting atom is one of ordinary hydrogen-1 (protium), of hydrogen-2 (deuterium) or of hydrogen-3 (tritium). The difference amounts to about one part in three thousand going from protium to deuterium, and an additional one part in ten thousand going from deuterium to tritium, as shown in Table 1:

TABLE 1

| Isotope | $\mathscr{R}$ | $\alpha$ | $\beta$ |
|---------|---------------|----------|---------|
| H       | 10967757.6    | 656.28   | 486.13  |
| D       | 10970743.6    | 656.10   | 486.00  |
| T       | 10971739.3    | 656.04   | 485.96  |

| Isotope | $\gamma$ | $\delta$ | $\epsilon$ | $\zeta$ |
|---------|----------|----------|------------|---------|
| H       | 434.05   | 410.17   | 397.01     | 388.91  |
| D       | 433.93   | 410.06   | 386.90     | 388.80  |
| T       | 433.89   | 410.03   | 386.86     | 388.77  |

This difference is well within the detection range of precision spectroscopes currently in use. In fact, the predicted existence of deuterium was first confirmed through the appearance of a faint companion line, at slightly shorter wavelength, beside each of the visible Balmer series lines.

For adequate separation of these closely spaced lines using a general-purpose spectroscope, however, a very long light path is needed since the angular difference produced by an ordinary prism or diffraction grating is very small. This is true because the optical dispersion, or change in refractive index as a function of wavelength, is quite small and gradual in nearly all ordinary glasses and other transparent substances.

Much higher, so-called "anomalous" dispersion can be obtained in certain materials over narrow spectral ranges. In a material having a narrow optical absorption band, the change in refractive index with wavelength becomes quite sharp in the immediate area of the band. Typically, the slope of the function of refractive index versus wavelength reverses direction within the band, spanning the wavelengths at which absorption has one-half or more of its maximum value, while areas of normal but much steepened slope lie to both sides.

Narrow visible-light absorption bands appear in liquid and solid solutions of various materials, including the trivalent ions of rare-earth metals. Didymium glass, for instance, is a solid solution of both neodymium and praseodymium oxides, and very strongly absorbs light in a narrow band between 570 and 595 nm while remaining nearly transparent at other visible wavelengths. Since this band coincides with the strong sodium emission lines at 589.0 and 589.6 nm, didymium glass is often used in the lenses of glassblowers' goggles.

Although didymium glass has no absorption bands suitably placed to heighten the dispersion of light at any of the visible hydrogen emission lines, alternative materials, perhaps combinations of rare-earth compounds or other materials in a matrix of glass, synthetic crystal, plastic, or water-holding gel, can be found having the required anomalous dispersion. Aqeuous praseodymium solutions, for instance, show strong peaks at wavelengths likely to give "anomalous" dispersion at both the $\beta$ and $\gamma$ lines of the Balmer series. Experimentation known to those of ordinary skill in the art can identify and develop a high-dispersion material having anomalous dispersion at the wavelengths needed.

Because anomalous dispersion takes place only on the edges of strong absorption peaks, it will likely be necessary to minimize the distance which light has to travel through the dispersive material so as to reduce the amount of absorption of the light at the wavelengths of interest. A Fresnel prism, analogous to the well-known Fresnel lens, can be made by forming a series of sawtooth ridges on one or both sides of a sheet of transparent material. This structure should not be confused with a diffraction grating, which works by a very different mechanism. Each ridge of the Fresnel prism acts as a mini-prism, bending and dispersing light. Although some diffraction also occurs in a parallel-ridge structure of this type, it should not pose any problem in this application, provided that ridge dimensions are large compared with the wavelengths of light being dispersed.

Still greater dispersion could be attained, in a small volume of material and without excessive loss of energy to absorption or interfacial reflection, by stacking several Fresnel prisms together and filling the spaces between them with nonabsorbing transparent material having an approximately equal refractive index at the central wavelength of interest. Alternatively, the prism sheets are formed from conventional, transparent material, such as polystyrene, and assembled as a sandwich with the highly dispersive material, in the form of a liquid, solid or gel, having as nearly as possible the same refractive index at the central wavelength, making up the filling. This arrangement provides very high dispersion, yet minimizes light losses resulting from absorption by the dispersive material, from internal reflection and from diffraction by the parallel ridges of the prism structure.

A hydrogen isotopic analyzer according to the present invention comprises a vacuum system and inlet manifold, a glass tube in which sample gases would be subjected to electric discharge and would emit light, optionally a second such tube containing a reference mixture of gases, a slit or other means of defining the pattern of such light if the tube does not define the pattern of light or does not define it sufficiently, a filter to isolate the wavelengths of interest, a dispersive element preferably of the anomalous type discussed above, a focusing device, a detector or array of detectors, and signal-processing circuitry.

The vacuum system could be much smaller than that required for mass spectroscopy, since the volume to be evacuated would be many times smaller (consisting only of the discharge tube and inlet manifold), would need to be evacuated only once or twice per sample rather than continually, and would not need to be pumped down to such low pressures since satisfactory line emission occurs at pressures around 1 mm Hg: six orders of magnitude higher than those needed in mass spectroscopy. A simple, one-stage mechanical pump would therefore suffice. A cycle of pumping down to the pump's pressure limit (typically 0.01 mm Hg), admitting a purge gas at roughly atmospheric pressure, then pumping down again immediately prior to admitting a new sample, could be used in place of a single pump-down to lower pressure. Emission from remaining traces of a properly-selected purge gas would not interfere with the analysis. Argon, for instance, has no emission lines near the Balmer $\alpha$ line, while helium gas has none close to the Balmer $\beta$ and $\gamma$ lines.

The discharge tube is of similar form to an "Osram" spectrum tube (for example, Edmund Scientific Co. #60906), having enlarged ends containing metal electrodes and a narrow central portion in which current is concentrated to produce the visible discharge. However, the design is modified in several ways. The internal volume of the tube is kept as small as possible, to minimize sample size. Electrodes are either made from, or completely covered with, a metal such as gold which does not significantly absorb or retain hydrogen. Tubing attached to one end piece provides a means of attachment to the sample manifold.

The tube is made from borosilicate or other glass which does not have a strong tendency to adsorb water vapor. h Preferably, the tube is constructed with flat, transparent end plates and with electrodes taking the form of open rings coaxial with the tube so that light passes freely down the length of the tube and emerges from the ends, and one end is fully or partially mirrored, much like a gas laser tube. Although it is very unlikely that true laser action would take place, this design still permits a significant part of the tube's light output to leave as a small, relatively intense and roughly collimated beam which should need little, if any, reshaping before entering the spectroscope, effectively constituting a slightly spread-out point source, or "dot source", at the tube's end. If necessary, a slit may be used to select a narrower beam portion. Minimizing the tube size brings the added benefit of minimizing re-absorption of the emitted light by other atoms in the sample.

Light emitted by the sample enters the spectroscope through a filter that blocks all wavelengths except those of interest. Narrow passband filters suitable for such use in the case of both the hydrogen $\alpha$ and $\beta$ lines are widely used in photographing certain types of distant nebulae, whose light consists mainly of atomic hydrogen emissions; by blocking most light from non-nebular sources, the filters aid in photographing these dim objects.

Passing through the filter, the light then is refracted and dispersed by a prism or prism sandwich of the type previously described. To provide sufficient path length for the beams (representing various isotopes) to diverge, the composite beam could be folded back on itself once or several times, by front-surface mirrors. Lenses or concave mirrors are inserted into the light path as needed, so that at some point one or more images of the sample-tube "dot source", or of the slit if one is used, are sharply focused in a plane. Light detectors, such as photodiodes, are placed in this plane so as to detect the light emitted by each of the isotopes present. The intensity of the beam representing each of the three isotopes shows the relative amount of that isotope in the sample.

Since samples are not consumed in the process of analysis, as they are in mass spectroscopy, heavy hydrogen isotopes are easily reclaimed after analysis. This could be done, for example, by opening the discharge tube to a chamber containing a lanthanum-nickel alloy, such as $LaNi_5$, in the form of powder or fine shavings. This material quickly absorbs the hydrogen, forming a tightly bound hydride with low equilibrium hydrogen pressure. Collection efficiency could be enhanced by cooling the alloy, further reducing the equilibrium pressure. Later, the isotopes can be recovered by removing the hydride to a suitable vessel and heating it to free the hydrogen.

A specific embodiment of the invention, using the visible blue-green $\beta$ line of the hydrogen emission spectrum, is illustrated in schematic form in FIG. 1. Samples are admitted through tube 10 and valve 12 to metering volume 14, which communicates through valve 16 with manifold 18. Also connected to manifold 18 are: hydrogen recovery vessel 20, containing lanthanum-nickel alloy shavings 22, and connected through valves 24 and 26 and removable coupling 28; purge-gas cylinder 30, connected through valves 32 and 34 and metering volume 36; vacuum pump 38, connected through valve 40; and discharge tube 42. All tubing and valves are minimum-volume types, suitable for vacuum service, and made from materials of low permeability to hydrogen. Tubing runs are kept as short as possible. Metering volume 14 is preferably smaller than volume 36. The two metering volumes are fitted respectively with pressure transducers 44 and 46, the former more sensitive than the latter.

Discharge tube 42 is of the design previously described. Mounted directly behind it, and sharing the same major axis, is a second tube 50, similar in all respects save that it is sealed and contains a reference gas, preferably a mixture of hydrogen and deuterium in equal amounts. These two discharge tubes are powered respectively by high-voltage, current-limited DC supplies 52 and 54. Mirror 56, preferably slightly concave, is mounted behind tube 50 in such a way that light leaving through the rear window of either tube is reflected back along the main axis to the front. Alternatively, the rear window of tube 50 may simply be silvered.

Figure 2:
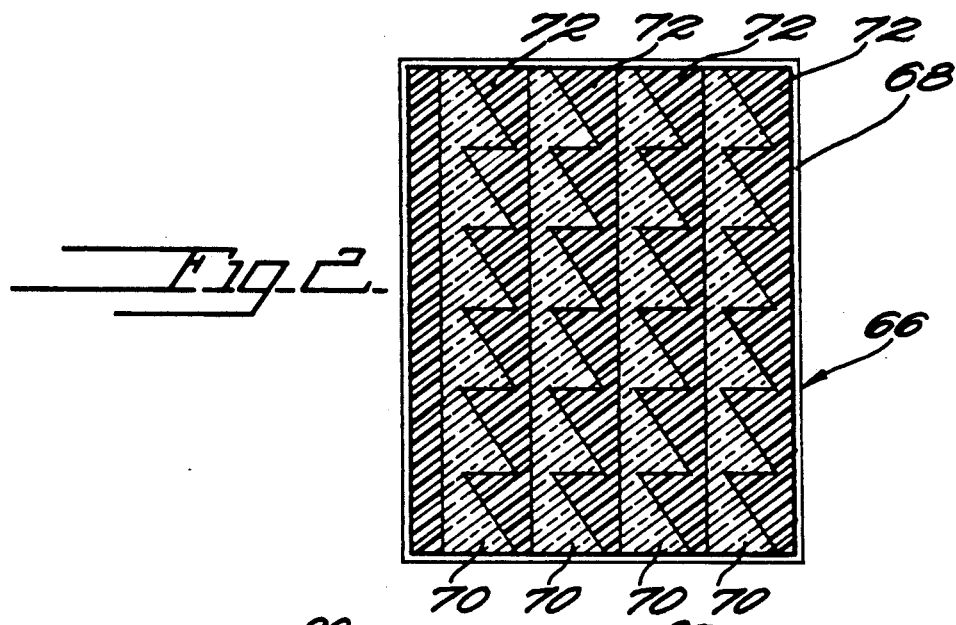
FIG. 2 is a detailed view of the Fresnel lens according to a preferred embodiment of the present invention.
Figure 3A:
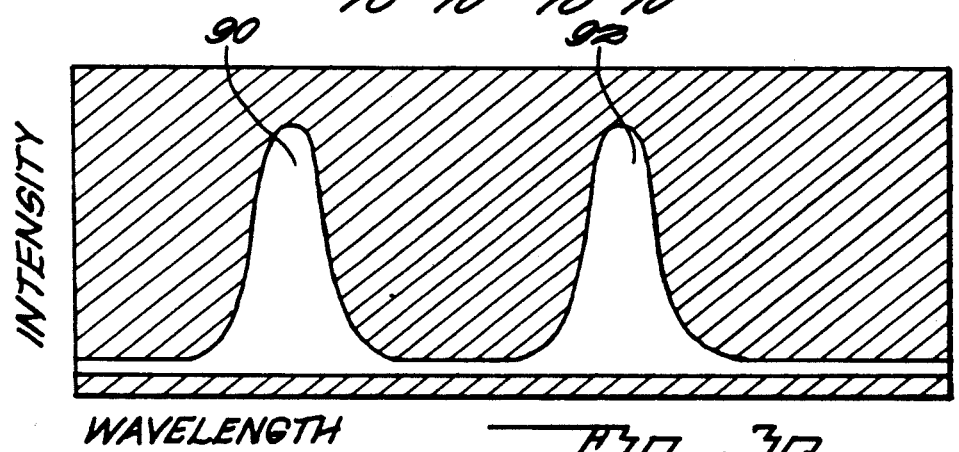
FIG. 3a and 3b are graphs of intensity of output versus wavelength illustrating the intensities of different isotopes of hydrogen in two samples.
Figure 3B:
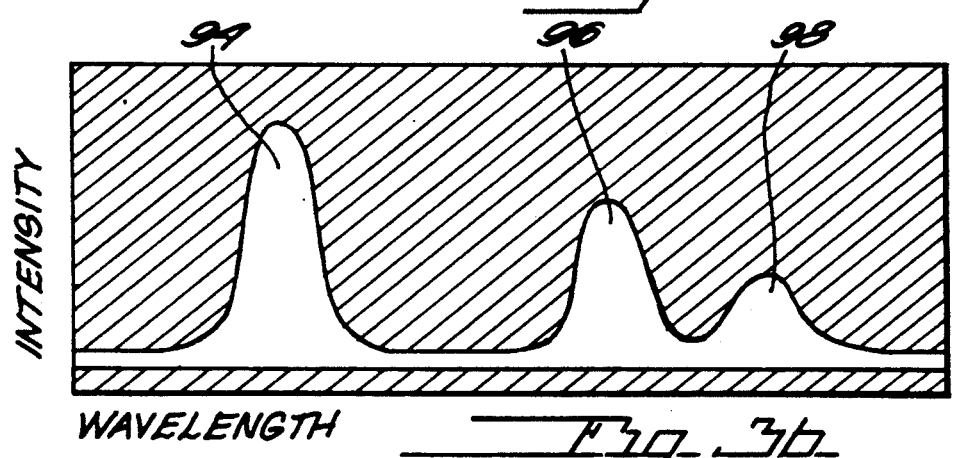

Light from tubes 42 and 50 passes through an adjustable slit 60, thereby entering a light-tight housing 62 which is lined with light-absorbing material. Located just inside this housing and opposite slit 60 are a filter 64, which passes light only in a narrow band surrounding the hydrogen $\beta$ line at 486.13 nm, and a multi-layer Fresnel prism 66. Prism 66 consists of a polystyrene case 68 (see FIG. 2) containing a plurality of stacked multi-prism plates 70, also composed of polystyrene. Within case 68, and filling all spaces between it and plates 70 and between one plate 70 and the next, is a clear, water-bearing liquid or gel 72 containing a praseodymium salt, adjusted to have a refractive index roughly equal to that of polystyrene at 486.13 nm yet, because of the strong praseodymium absorption line centered at 481 nm, having much greater dispersion.

Passing through prism 66, light rays 74 representing $\beta$ line emission are bent only slightly, yet the three wavelengths 74a, 74b, and 74c representing the three isotopes are separated and follow slightly different paths. Front-surface mirrors 76, 78, 80 and 82 bend rays 74 back on themselves, providing a long light path within a relatively small housing. Mirror 78 is made concave and adjustable by means of fine-pitched screws 84, so as to focus the image of slit 60 on a detector array 86 composed of a large number of silicon photodiodes.

This image is composed of one, two or three peaks whose intensities represent the abundances of the three hydrogen isotopes in the sample or in the reference tube. Since temperature is likely to have some effect on the shape and intensity of the 481 nm praseodymium absorbance peak and thus on dispersion, self-calibration is performed during each analysis by alternatively energizing sample tube 42 and reference tube 50. Sample tube 42 produces two equal peaks 90 and 92, representing hydrogen and deuterium in equal amounts. A sample containing all three hydrogen isotopes produces three peaks 94, 96, and 98, two of which match peaks 90 and 92 and the third of which, corresponding to tritium, does not. An appropriate signal-conditioning and signal-analysis system, preferably incorporating a small computer 100, performs this comparison, quantifies the intensities of peaks 94, 96, and 98, and from them deduces the ratios of the three hydrogen isotopes in the sample.

During analysis, valves 12, 16, 24, 26, 32, 34, and 40 are closed. For sample changing, a multistep procedure is used, with specific combinations of these valves opening and closing in turn. This could be done under the control of the same computer used for sample analysis.

If the sample is to be saved for recovery of heavy hydrogen isotopes, valves 16, 24, and 26 are opened, and hydrogen is absorbed into the lanthanum-nickel alloy 22 held in vessel 20, while the remaining pressure is monitored by transducer 44 mounted in chamber 14. When the pressure has stabilized, indicating that hydrogen absorption has ceased, the valves are closed again; vessel 20 may then be removed at connector 28 and taken to a recycling facility where hydrogen isotopes may be freed from the metal by heating. If the sample is not to be saved, this step may be omitted.

If residual pressure in manifold 18 is above the minimum attainable with pump 38, then pump 38 is started and valves 16, 34, and 40 are opened so that manifold 18, metering volumes 14 and 36 and sample tube 42 may be evacuated. When transducer 44 indicates that the minimum pressure (typically 0.01 mm Hg) has been reached, valves 34 and 40 are closed and valve 32 is opened, admitting very pure, dry helium purge gas to metering volume 36 where its pressure is monitored by transducer 46. Pump 38 continues to run.

Upon attainment of roughly atmospheric pressure, valve 32 and preferably valve 16 are closed and valve 34 is opened, admitting the purge gas to the parts of the apparatus previously evacuated. Valve 34 provides an extra margin of assurance that uncontrolled pressurization of the manifold and sample tube will not take place. Closing valve 16 before purge prevents shock damage to transducer 44.

Turbulence resulting from the admission of purge gas through valve 34 causes thorough mixing with any residual gas from the sample. Valve 16 is then opened, letting the purge gas (now at lower pressure) into volume 14. Next, valve 40 is re-opened, and manifold 18, sample tube 42 and metering volumes 14 and 36 are re-evacuated to the minimum attainable pressure. This "purge-and-pump" cycle may be repeated, if desired, to remove any trace gases remaining from the previous sample or to purge any leaked-in atmospheric gases immediately prior to running a new sample.

After pumpdown, all valves are closed and the pump is turned off. A new sample may then be admitted by opening valve 12, allowing gas containing hydrogen isotopes to enter metering chamber 14, where the pressure is monitored by transducer 44. When the amount of gas in chamber 14 is adequate, valve 12 is closed and valve 16 is opened, and the gas flows into manifold 18 and sample tube 42, exerting a pressure in the range of 0.5 to 1.0 mm Hg. The gas is then subjected to electric discharge, and its isotopic composition is measured in the manner described above.

It will be apparent to those skilled in the art that many changes and substitutions can be made to the preferred embodiment herein described without departing from the spirit and scope of the present invention as defined by the appended claims.

What is claimed is:

1. Apparatus for analysis of isotopes of a sample of hydrogen gas, said isotopes characterized by an emission spectrum including Balmer series with beta and gamma lines, said apparatus comprising:
    means for exciting at least some electrons in said sample to a higher energy state from a lower energy state so that at least some electrons cause the emission of light when in transition from said higher energy state to said lower energy state;
    dispersing means in spaced relation to said exciting means for receiving said light and for dispersing said light according to wavelength, said dispersing means including a prism made of an anomalously dispersing material,
    said anomalously dispersing material selected to disperse said light to a greater extent at frequencies near said beta and gamma lines of said Balmer series than at higher and lower frequencies; and
    detecting means in spaced relation to said dispersing means for receiving said dispersed light and for detecting the amounts of said light as a function of wavelength, said detecting means producing an output responsive to said amounts,
    said output indicating of the quantity and type of said isotopes of hydrogen present in said sample. u 2. The apparatus as recited in claim 1, wherein said dispersing means further comprises a plurality of layers, each layer composed of a dispersive material and a non-absorbing transmitting material, said dispersive material having a series of ridges formed therein.

3. The apparatus as recited in claim 1, further comprising:
    a chamber having an interior;
    means for introducing said sample into said interior;
    means for reducing the pressure in said interior; and
    means for creating an electrical discharge in said interior in the presence of said sample.

4. The apparatus as recited in claim 1, further comprising means in communication with said detecting means for processing said output.

5. The apparatus as recited in claim 1, further comprising means in communication with said exciting means for recovering said sample.

6. The apparatus as recited in claim 1, wherein said detecting means further comprises:
    an array of photodiodes; and
    means for focusing said dispersed light onto said array.

7. Apparatus for analysis of isotopes of a sample of hydrogen gas, said apparatus comprising:
    a chamber having an interior;
    means for introducing said sample into said interior;
    means for reducing the pressure in said interior;
    means for creating an electrical discharge in said interior in the presence of said sample to excite at least some electrons of said sample to higher energy states from lower energy states so that said at least some electrons of said sample cause the emission of light when in transition from said higher energy states to said lower energy states;
    dispersing means in spaced relation to said exciting means for receiving said light and for dispersing said light according to wavelength, said dispersing means including a prism made of an anomalously dispersing material;
    said anomalously dispersing material selected to disperse said light to a greater extent at frequencies near said beta and gamma lines of said Balmer series than at higher and lower frequencies; and
    an array of photodiodes;
    means in spaced relation to said dispersing means for focusing said light onto said array, said array producing an output responsive to said light; and
    means in electrical connection with said array for processing said output to calculate the quantity and type of said isotopes of hydrogen present in said sample.

8. The apparatus as recited in claim 7, wherein said dispersing means further comprises:
    a plurality of sheets of a first material, each of said plurality of sheets having a series of sawtoothed ridges, said plurality of sheets arranged in a stack; and
    a second material placed between sheets of said first material.

9. The apparatus as recited in claim 8, wherein said first material is anomalously dispersive and said second material does not absorb said light.

10. The apparatus as recited in claim 8, wherein said second material is anomalously dispersive and said first material does not absorb said light.

11. The apparatus as recited in claim 7, further comprising means in communication with said chamber for recovering said sample.

12. The apparatus as recited in claim 11, wherein said recovering means includes a metal hydride for absorbing said sample.

13. Apparatus for analysis of isotopes of a sample of hydrogen gas, said apparatus comprising:
    a chamber having an interior;
    means for introducing said sample into said interior;
    a vacuum pump in communication with said interior for reducing the pressure of said interior of said chamber;
    means for creating an electrical discharge in said interior in the presence of said sample to excite at least some electrons of said sample to higher energy states from lower energy states so that said at least some electrons of said sample cause the emission of light when in transition from said higher energy states to said lower energy states;
    filter means in spaced relation to said creating means for receiving said light and passing a portion of said light;
    dispersing means in spaced relation to said filter means for receiving said portion of said light and for dispersing said portion according to wavelength, said dispersing means anomalously dispersing light having wavelengths characteristic of said portion,
    said dispersing means made of an anomalously dispersing material selected to disperse said light to a greater extent at frequencies near said beta and gamma lines of said Balmer series than at higher and lower frequencies;

an array of photodiodes;

means in spaced relation to said dispersing means for focusing said dispersed portion onto said array, said array producing an output responsive to said portion; and means in electrical connection with said array for processing said output to calculate the quantity and type of said isotopes of hydrogen present in said sample.

14. The apparatus as recited in claim 13, wherein said portion passed by said filter means includes one of the lines of the Balmer series.

15. The apparatus as recited in claim 13, wherein said dispersing means further comprises:

a plurality of sheets of a first material, each of said plurality of sheets having a series of sawtoothed ridges, said plurality of sheets arranged in a stack, said first material being anomalously dispersive to said portion; and a second material placed between sheets of said first material, said second material being transparent to said portion.

16. The apparatus as recited in claim 13, wherein said dispersing means further comprises:

a plurality of sheets of a first material, each of said plurality of sheets having a series of sawtoothed ridges, said plurality of sheets arranged in a stack, said first material being transparent to said portion; and a second material placed between sheets of said first material, said second material being anomalously dispersive to said portion.

17. The apparatus as recited in claim 13, further comprising means in communication with the interior of said chamber for recovering said sample.

18. The apparatus as recited in claim 17, wherein said recovering means includes a metal hydride for absorbing said sample.

* * * * *